US011833184B1

(12) United States Patent
Nguyen (10) Patent No.: US 11,833,184 B1
(45) Date of Patent: Dec. 5, 2023

(54) FREEZE-DRIED NIPA PALM POWDER AND METHOD OF MANUFACTURING THE SAME

(71) Applicant: Vien Lam Nguyen, Ho Chi Minh (VN)

(72) Inventor: Vien Lam Nguyen, Ho Chi Minh (VN)

(73) Assignee: VINAMIT JSC., Binh Duong (VN)

( * ) Notice: Subject to any disclaimer, the term of this patent is extended or adjusted under 35 U.S.C. 154(b) by 0 days.

(21) Appl. No.: 18/343,765

(22) Filed: Jun. 29, 2023

(51) Int. Cl.
| | |
|---|---|
| *A61K 36/00* | (2006.01) |
| *A61K 36/889* | (2006.01) |
| *A61K 36/752* | (2006.01) |
| *A61K 36/725* | (2006.01) |
| *A61K 36/73* | (2006.01) |
| *A61K 36/9068* | (2006.01) |
| *A61K 35/747* | (2015.01) |
| *A61K 35/744* | (2015.01) |
| *A61K 35/745* | (2015.01) |
| *A01G 23/14* | (2006.01) |
| *A23L 33/105* | (2016.01) |
| *A23L 33/135* | (2016.01) |
| *A61K 9/19* | (2006.01) |
| *A61K 36/22* | (2006.01) |
| *A61K 35/00* | (2006.01) |

(52) U.S. Cl.
CPC ............ *A61K 36/889* (2013.01); *A01G 23/14* (2013.01); *A23L 33/105* (2016.08); *A23L 33/135* (2016.08); *A61K 9/19* (2013.01); *A61K 35/744* (2013.01); *A61K 35/745* (2013.01); *A61K 35/747* (2013.01); *A61K 36/22* (2013.01); *A61K 36/725* (2013.01); *A61K 36/73* (2013.01); *A61K 36/752* (2013.01); *A61K 36/9068* (2013.01); *A23V 2400/113* (2023.08); *A23V 2400/21* (2023.08); *A23V 2400/517* (2023.08); *A23V 2400/535* (2023.08); *A61K 2035/115* (2013.01); *A61K 2236/11* (2013.01); *A61K 2236/15* (2013.01); *A61K 2236/31* (2013.01)

(58) Field of Classification Search
CPC ............................... A61K 9/19; A61K 36/889
See application file for complete search history.

*Primary Examiner* — Qiuwen Mi (57) ABSTRACT

A freeze-dried nipa palm powder obtainted by mixing (75-100) part of a sap of inflorescence stalk with (0-25) part other ingredients, then freezing said sap of inflorescence stalk with said other ingredients in frozen molds using an individual quick freezer (IQF) at temperature from $-25°$ C. to $-29°$ C. to obtain frozen sap of inflorescence stalk blocks, and freeze drying frozen sap of inflorescence stalk molds at a pressure of $7.8948 \times 10^{-4}$–$1.3158 \times 10^{-3}$ atm for 48 hours. The freeze-dried nipa palm powder such as multi-purpose food products that can be used not only as directly, or dissolved in water such as a beverage, but also as a health-promoting functional food, improve immunity, skin care, and beauty for users.

10 Claims, 1 Drawing Sheet

FREEZE-DRIED NIPA PALM POWDER AND METHOD OF MANUFACTURING THE SAME

FIELD OF THE INVENTION

The present invention relates to the field of food processing. In particular, the invention relates to multi-purpose food products that can be used not only as directly, or dissolved in water such as a beverage, but also as a functional food to promote health, improve immunity, skin care, and beauty for users. More specifically, the present invention relates to freeze-dried nipa palm powder and method of manufacturing the same.

BACKGROUND ART

Nipa palm (*Nypa fruticans* Wurmb.) is distributed mainly in the tropics, in about 10 degrees Northern and Southern Hemisphere, stretching from Sri-Lanka, through the Southeast to northern Australia. In the early 20th century, Nipa palm was introduced into West African countries. Some countries have the largest area of Nipa palm in the world such as Indonesia (700.000 ha), Papua New Guinea (500.000 ha) and the Philippines (8,000 ha). In Southeast Asian countries, Nipa palm is grown instead of growing naturally like some other places (World Agro Forestry). In the Mekong Delta, although there are no official statistics on the area planted to Nipa palm, but Nipa palm trees are planted a lot along rivers and canals in the waters of provinces such as Long An, Tien Giang, Ben Tre, Tra Vinh, Soc Trang, Hau Giang, Bac Lieu, Ca Mau, and Kien Giang. According to Faparusi (1986), Nipa palm is a tree with many uses and can be used for many different purposes: leaves and sheaths can serve for construction; fruit used for food; the Nipa palm sap can be used to process sugar, vinegar, alcohol and bio-alcohol. In countries such as the Philippines, Malaysia, and Thailand, the Nipa palm sap is mainly used to produce bioethanol, while in the Americas and Africa it is used to make alcohol (Dalibard, 1999). Nipa palm sap has a very high sugar content of 16.4% w/v, while sugarcane is only about 12% w/v. If well managed, the yield of sugar from nipa palm can reach 15-20 tons/ha compared to sugarcane with only 5-15 tons/ha/year (Van Dieu, 1974). The time for harvesting the Arecaceae family sap varies depending on the species, with some species only harvesting the resin once while the nipa palm can be harvested for up to 50 years (Abedin et al., 1987).

In the government's new project to plant 5 million hectares of forest (Program 661), nipa palm ranks second among 10 trees selected for planting protection forests to break waves and protect wetlands (Nguyen Ngoc Binh, 2004). In the context of global climate change, the water level in the Mekong Delta may rise, the more widespread the risk of saltwater intrusion, the more potential exploitation of food from the nipa palm can grow well in the environment brackish water and not too salty water (Das and Siddiqi 1985; Siddiqi, 1995) is a matter of necessity. Some comparative characteristics between more saps for sugar processing show that nipa palm is the optimal source of raw materials, listed in Table 1 below.

TABLE 1

Comparative characteristics between more saps for sugar processing

| Character-istics | More saps for sugar processing | | | |
|---|---|---|---|---|
| | Nipa palm | Coconut | Palmyra palm | sugarcane |
| Fructose content | 14%-17% | 14%-16% | 13%-15% | 11% |
| Age to start mining | from year 5 | from year 8 | from year 15 | Six months |
| Mining time | 50 year | 20-30 year | 70 year | |
| Amount of sap from inflorescence (mL/day) | 600-800 | 600-800 | 1,000 | — |
| Tree density (ha) | 625 trees (density 4×4 m) | 400 trees (density 5×5 m) | 400 trees (density 5×5 m) | — |
| Area | about 20.000 ha | 138,000 ha (Ben Tre 51,000 ha) | 60.000 cây Vùng Bay Nui An Giang | — |
| Sugar yield | 20 tons/ha | 15-20 tons/ha | 90 kg/tree/year | 5-15 tons/ha |
| Sap mining time | Year round | From November to May next year | From November to May next year | — |
| Ethanol production | 6,480 L/ha | No | No | 4,550 L/ha |

Nipa palm sap is a white liquid produced from the extraction process of the nipa inflorescence. It is a very sweet natural product. Nipa palm sap is good for health and is believed to provide some protection for the human body (Gupta et al., 1980). Nipa palm sap can be used as a raw material for the production of sugar (Paivoke, 1985) and can also be used in the production of vinegar (Hamilton and Murphy, 1988), a distilled or fermented beverage known as "tuba" or "soom" in the Philippines, "arak" or "tuak" in Indonesia, "toddy" in Malaysia, India and Bangladesh (Hamilton and Murphy, 1988). Nipa palm is also a useful raw material for biofuel production. It can produce higher ethanol than sugarcane (6,480–10.224 L/ha/year vs 3,350-6,700 L/ha/year) (Hamilton and Murphy, 1988).

There are many methods used to nipa palm sap, depending on the country. The basis used to exploit nipa inflorescence is to use impact measures aimed at making the flower stalks hurt such as kick at the base of the flower stalk, hit along the length of the flower stalk, and twist the neck of the flower stalk. If applied once a week, continuously for 12 weeks will give an average yield of 155 mL/24 hours/plant in 01 month; while acting 3-5 times/week, in 5-12 weeks will give an average yield of 1,300 mL of sap. To start harvesting, the nipa inflorescence was cut from the stalk and renewed the cut twice a day, removed 2-3 slices with a thickness of about 1-2 mm, and continued until the peduncle was too short to cut. The sap is collected into bamboo tubes one or two internodes long. The bamboo tubes are sealed at both ends, but have a hole in the top to insert the flower stalk. Yields were collected daily at 2 times, that is, 9-10 am and 3-4 pm.

Another factor affecting the quality of nipa palm sap is the number of fungi, bacteria and total aerobic microorganisms present in the nipa palm sap at different harvesting times. The rapid increase in the total number of microorganisms in the nipa palm sap is due to the fact that microorganisms use the sugar in the sap to carry out the fermentation process (Chanthachum and Beuchat, 1997). Microorganisms in the nipa palm sap grow very quickly, causing the quality of the sap to seriously decrease and become unusable after a short time. From there, it shows that the time of harvesting nipa palm sap greatly affects the quality. Therefore, it is best to harvest the nipa palm sap from one to four hours after the flower stalk sap begins to secrete, and there should be a method to store it properly to limit the growth of microorganisms as well as maintain the quality of the nipa palm sap.

Currently, the source of raw materials for nipa palm sap is mainly for cooking sugar, fermenting alcohol and partly used as a fresh beverage for tourists. Nipa palm is abundant but the economic value is still low. Therefore, diversifying products from nipa palm, taking advantage of this raw material to create new products with high sensory value, ensuring food safety and hygiene is also one of the effective methods to enhance the value of this specialty source.

According to VN patent application No. VN1-2014-03305, the invention refers to the process of producing sap from the *Nypa* palm inflorescence, this process includes the following steps: apply bending force to bend the flower chamber stalk in a convenient direction to get sap so that when harvesting sap from the base up to the *Nypa* palm inflorescence is curved in a parabolic shape and the nipa inflorescence is tilted in a favorable direction for the impact and collection of sap; apply excitation force along the peduncle of the nipa flower chamber stalk on both the upper and lower surfaces to stimulate the circulation of the vascular bundle in the stalk; apply the stimulus at the base of the peduncle of the nipa flower chamber stalk to to stimulate the circulation of the vascular bundle in the stalk; cut the flower chamber stalk to collect sap from the cutting site, the sap will secrete from the cut site; and install sap containers tool at the cutting site. However, the time to harvest sap from the flower chamber stalk according to this invention is different from the present invention, specifically, after 4 to 5 weeks after the nipa tree flowers, the head inflorescence stalk is cut. Conduct "massage" of the inflorescence stalk for 2-3 days, and then harvest the sap from the inflorescence stalk, and at the same time, the above present invention proposes to choose a method of processing the sap from the inflorescence stalk to prolong time preservation but still retain the traditional taste.

According to VN patent application No. VN2-2022-00022, the invention refers to the process of manufacturing concentrated nipa powder from the nipa palm tree. The concentrated nipa powder obtained in a useful concentrated is less prone to change during harvesting and manufacturing process, while retaining the high content of nutrients and healthful compounds of the nipa powder, creating products of high quality and meeting the needs of consumers. However, products processed by the method of concentration often darken, change in taste, and lose vitamins and nutrients.

According to KR patent application No. KR20200030230, the invention refers to an oral composition containing: (a) a *Nypa fruticans* extract; (b) a fluorinated compound, a surfactant, or both. Specifically, the present invention relates to a composition for oral care which is harmless to the human body and has an excellent anti-inflammatory effect, thereby being able to be used for preventing or treating various oral diseases such as periodontal disease, bad breath, etc. By using the composition, it is possible to manufacture and use products for oral use that can be safely and continuously used.

According to KR patent application No. KR101710193, the invention refers to a method for producing a functional grain using flower stalks of nipa palm, and to a functional grain by the method. More specifically, the method for producing the functional grain using flower stalks of nipa palm comprises the following steps: extracting active components from flower stalks of nipa palm; concentrating the acquired extract; cleaning grain and then drying the same; and coating the dried grain with the concentrated extract. According to the present invention, the functional grain exhibits outstanding antioxidant and anti-inflammatory efficacy, and thus promotes health of users. Consumption of grain can be accelerated owing to enriched flavors of the grain, thereby increasing rural household incomes.

The above inventions meet the specific purposes and requirements of a technical solution. However, the disclosure of the invention does not refer to the method of processing the sap of inflorescence stalk by freeze-dried technique, and at the same time, the method of optimizing the collection of the sap of inflorescence stalk has high efficiency, preventing the invasion of microorganisms during the harvest is also not disclosed, or there is disclosed but with a difference. Moreover, the technical solutions mentioned above do not mention the addition of fruit ingredients, ginger ingredients, and Probiotics ingredients, which are admixed to the sap of inflorescence stalk.

Therefore, what is needed is a method that can convert the sap of nipa inflorescence stalk to concentrated powder which is chemically stable, has a long shelve life, short reconstitution time with excellent potency levels—the original fragrance, nutrients, vitamins, color are preserved.

What is needed is a method of selecting, preparing the sap of nipa inflorescence stalk to mechanically act according to predefined guidelines for the purpose of obtaining high-performance sap of inflorescence stalk and preventing fermentation of sap.

Furthermore, what is needed is a freeze-dried nipa palm powder that includes probiotics so that it is easy to digest after reconstitution by mixing with water.

Yet, what is needed is a freeze-dried nipa palm powder that has a low glycemic index of 35 compared to sugarcane or sugarcane juice with a glycemic count of 80; has a stable control effect on blood sugar for users who do not have or have diabetes.

Finally, what is needed is a method of manufacturing freeze-dried nipa palm powder that includes simple steps, is suitable for industrial scale production, and does not pollute the environment.

This invention provides solutions to achieve the above goals.

SUMMARY OF THE INVENTION

Accordingly, an objective of the present invention is to provide a freeze-dried nipa palm powder obtainted by mixing (75-100) part of a sap of inflorescence stalk with (0-25) part other ingredients, then freezing said sap of inflorescence stalk with said other ingredients in frozen molds using an individual quick freezer (IQF) at temperature from $-25°$ C. to $-29°$ C. to obtain frozen sap of inflorescence stalk blocks, and freeze drying frozen sap of inflorescence stalk molds at a pressure of $7.8948 \times 10^{-4} - 1.3158 \times 10^{-3}$ atm for 48 hours;

wherein the sap of inflorescence stalk having a pH of 6-7, which has been filtered to remove impurities, has been heat treated, and has been added a salt (NaCl) at the rate of (1000-1500) of the sap of inflorescence stalk with 1 part of the salt;

wherein the other ingredients selected from the one or more of the following: a fruit ingredient, a ginger ingredient, a probiotic ingredient, and a combination thereof;

wherein the probiotic ingredient comprising *Lactobacillus, Streptococcus*, and *Bifidobacterium*;

Another objective of the present invention is to provide a freeze-dried nipa palm powder according to the first formula comprising: 100 part of the sap of inflorescence stalk, 0 part the fruit ingredient, 0 part the ginger ingredient, and 0 part the probiotic ingredient.

Yet another objective of the present invention is to provide a freeze-dried nipa palm powder according to the second formula comprising: (75-90) part of the sap of inflorescence stalk, (10-25) part the fruit ingredient, 0 part the ginger ingredient, and 0 part the probiotic ingredient.

Another objective of the present invention is to provide a freeze-dried nipa palm powder according to the third formula comprising: (95-100) part of the sap of inflorescence stalk, 0 part the fruit ingredient, (1-5) part the ginger ingredient, and 0 part the probiotic ingredient.

Another objective of the present invention is to provide a freeze-dried nipa palm powder according to the fourth formula comprising: 100 part of the sap of inflorescence stalk, 0 part the fruit ingredient, 0 part the ginger ingredient, and (0.1-0.7) part the probiotic ingredient.

In view of the foregoing, another objective of the present invention is to provide a freeze-dried nipa palm powder according to the fifth formula comprising: (75-90) part of the sap of inflorescence stalk, (10-25) part the fruit ingredient, 0 part the ginger ingredient, and (0.1-0.7) part the probiotic ingredient.

Another purpose of the invention is to provide a freeze-dried nipa palm powder containing many vitamins, electrolytes, supports the maintenance of water in the body, blood pH level and muscle function, works to prevent cramps or muscle spasms.

Another purpose of the invention is to provide a method of manufacturing a freeze-dried nipa palm powder, which retains the original color and taste, minimizes nutritional loss (lower than 5%), does not contain fat, no cholesterol and has natural sweetness suitable to replace sweeteners for people with type 2 diabetes.

Finally, the purpose of the invention is to provide a method of manufacturing a freeze-dried nipa palm powder comprising steps performed in the following specific orders:
(i) Preparing materials including (75-100) part of a sap of inflorescence stalk, and (0-25) part other ingredients;
wherein the other ingredients selected from the one or more of the following: a fruit ingredient, a ginger ingredient, a probiotic ingredient, and a combination thereof;
wherein the sap of inflorescence stalk is obtained by performed in a specific order from (a') to (c') comprising:
(a') choosing Nipa palm trees (*Nypa fruticans* Wurmb.) having 5 years old or more, and cleaning around the Nipa palm trees;
monitoring the Nipa palm trees after flowering for 4-5 weeks, then cutting a slice of the head of a inflorescence stalk thick 1-2 mm; wherein said cut position of the head of the inflorescence stalk forms is an inclined plane with an angle of 30°-45°;
using PE bags (Polyethylene plastic bags) to cover the position of the head of the said cut the inflorescence stalk;
(b') mechanical impacting on the inflorescence stalk (a') in the order of steps from (A) to (C) includes:
(A) appling a coffee grounds solution evenly on the inflorescence stalk, and bending the inflorescence stalk 5 times in the same direction; wherein the coffee grounds solution is obtained by dissolving a ratio of a coffeegrounds having moisture content less than 18% and water having 1:(2-3);

(B) knocking the inflorescence stalk by a part wooden slats covered with cloth; wherein the wooden slats covered with cloth having the following characteristics: 35 cm long, 3.5 cm wide, 1.5 cm thick, and ½ the length of the wooden slats is covered by a 1 cm thick cloth;
knocking evenly with light force in the direction perpendicular to a surface of the inflorescence stalk, and combining translational movement of knocking along the inflorescence stalk; wherein the surface of the inflorescence stalk includes an upper surface of the inflorescence stalk, a lower surface of the inflorescence stalk, an inner surface of the inflorescence stalk, and an outer surface of the inflorescence stalk; and
wherein a time of knocking time for each inflorescence stalk is 1 min;
(C) rubbing/clawing the inflorescence stalk by the palm and fingers of hands with light force, and combining translational movement rubbing/clawing along the inflorescence stalk for 1 min; wherein the hands are covered by gloves;
wherein performing steps from (A) to (C) at the frequency of 1 time/day until the inflorescence stalk starts to sap, then move to step (c');
(c') collecting the sap of inflorescence stalk by following the steps from (A') to (E') including:
(A') opening the PE bags containing the sap of inflorescence stalk from the head of the inflorescence stalk, and sealing a mouth of the PE bags, then storing in container containing gel ice packs in the ratio of 1 part the gel ice packs to (3-5) parts the PE bags containing the sap of inflorescence stalk;
wherein the maximum storage time is 12 hours;
wherein the gel ice pack has been frozen for at least 8 hours;
(B') cutting a slice of the inflorescence stalk having thick 1-2 mm at the head position of the inflorescence stalk that turned brown, then using the PE bags to cover to the position of the head of the said cut the inflorescence stalk;
wherein said cut position of the head of the inflorescence stalk forms is an inclined plane with an angle of 30°-45°;
(C') appling a coffee grounds solution evenly on the inflorescence stalk, and bending the inflorescence stalk 5 times in the same direction; wherein the coffee grounds solution is obtained by dissolving a ratio of a coffee grounds having moisture content less than 18% and water having 1:(2-3);
(D') knocking the inflorescence stalk by a part wooden slats covered with cloth; wherein the wooden slats covered with cloth having the following characteristics: 35 cm long, 3.5 cm wide, 1.5 cm thick, and ½ the length of the wooden slats is covered by a 1 cm thick cloth;
knocking evenly with light force in the direction perpendicular to a surface of the inflorescence stalk, and combining translational movement of knocking along the inflorescence stalk; wherein the surface of the inflorescence stalk includes an upper surface of the inflorescence stalk, a lower surface of the inflorescence stalk, an inner surface of the inflorescence stalk, and an outer surface of the inflorescence stalk; and
wherein a time of knocking time for each inflorescence stalk is 1 min;
(E') rubbing/clawing the inflorescence stalk by the palm and fingers of hands with light force, and combining translational movement rubbing/clawing along the inflorescence stalk for 1 min; wherein the hands are covered by gloves;
wherein the collecting the sap of inflorescence stalk is selected from one of following at the frequency: 2 times/day, 3 times/day, and 4 times/day;

wherein each time of collecting the sap of inflorescence stalk are repeated in order from (A') to (E'), and the total time to collect the sap of inflorescence stalk in each inflorescence stalk is 30 days;

wherein the fruit ingredient selected from the one of the fruits including: strawberries (*Fragaria vesca* L.), mangoes (*Mangifera indica* L.), citrus fruits, and Indian jujubes (*Ziziphus mauritiana* L.); wherein said citrus fruits including grapefruit (*Citrus maxima, Citrus grandis* L.), kumquat (*Fortunella japonica* (Thunb.) Swingle, *Citrus japonica* Thunb.), lemon (*Citrus aurantifolia*), lime (*Citrus limon* (L.) Burm.f.—*Citrus medica* ssp. lomon L.), and orange (*Citrus sinensis* (L.) Osheck (*C. aurantium* L. var. *dulcis* L.);

wherein the fruit ingredient obtained by performed in a specific order comprising:

selecting and preparing fruits by a predetermined quality guideline, includes selecting said fruits that have a Brix level of at least 10, performing visual inspection to select ripe, which having heavy-handed, and undamaged fruits;

washing fruits, then taking the flesh of the fruits, and removing the fruits by-products;

squeezing the flesh of the fruits to obtained a fruits juice; and adjusting the Brix of the fruit juice to 15%-30% to obtained the fruit ingredient;

wherein the ginger ingredient obtained by performed in a specific order comprising:

selecting and preparing ginger (*Zingiber purpureum* Roscoe.) by a predetermined quality guideline, includes:

ginger obtained from ginger plants multiplicated by plant tissue culture technology; wherein at the budding stage using a suitable medium for in vitro multiplication of ginger shots includes: MS mineral, 30 g/L sucrose, 6.5 g/L agar, 1.5 mg/L BAP (6-Benzyl amino purine), 0.5 mg/L NAA (1-naphthalene acetic acid), and 150-200 ml/L of the sap of inflorescence stalk having a pH of 6-7;

hard ginger, has a characteristic aroma, is not moldy, does not germinate, is not damaged, does not have the bite of worms and insects;

squeezing ginger obtained a ginger residue;

puring the ginger residue; and adjusting the humidity of the ginger residue reaches 20%-25%;

wherein the probiotic ingredient comprising *Lactobacillus, Streptococcus*, and *Bifidobacterium*;

wherein said *Lactobacillus* selected from the one or more of the species including *Lactobacillus acidophilus* (the identifier on the gene bank is AB725355.1), *Lactobacillus acidophilus* (the identifier on the gene bank is MN173898.1), *Lactobacillus acidophilus* (the identifier on the gene bank is AB755424.1), and a combination thereof;

wherein said *Streptococcus* selected from the one or more of the species including *Streptococcus* sp. M40 (the identifier on the gene bank is AB262667.1), and *Streptococcus* sp. M62 (the identifier on the gene bank is AB262658.1), and a combination thereof;

wherein said *Bifidobacterium* selected from the one or more of the species including *Bifidobacterium bifidum* (the identifier on the gene bank is MZ596306.1), and *Bifidobacterium pseudocatenulatum* (the identifier on the gene bank is MW073427.1), and a combination thereof;

(ii) checking sensory and pH of the sap of inflorescence stalk;

if the sap of inflorescence stalk at step (i) has the following characteristics including: aroma of young and sweet nipa palm meat, no coagulation, the sap is clear yellow, pH is 6-7, then filtering the sap of inflorescence stalk at step (i) to create a filtrate by a sieve with a pore size of 0.045 mm;

otherwise, the sap of inflorescence stalk at step (i) does not have the said characteristics, it shall be removed;

(iii) considering whether to preserve the filtrate at step (ii);

if the filtrate at step (ii) does not need to to be processed immediately, then do step (iv);

otherwise, if the filtrate at step (ii) needs to be processed immediately, then do step (v);

(iv) preserving the filtrate at step (ii) by selecting one of two following option preserves depending on the time preservation, including:

a first option: preserving the filtrate at step (ii) at 2-4° C. for 3 days; and a second option: preserving the filtrate at step (ii) at $-18°$ C. for 6 months;

the result obtained at step (iv) is a filtrate for temporary preservation;

(v) heating the filtrate at step (ii)/the filtrate for temporary preservation at step (iv) at 20° C. to create a foundation solution;

(vi) mixing a salt (NaCl) with the foundation solution at step (v) to create a temporary filtrate; wherein a mixing ratio is (1000-1500) part of the sap of inflorescence stalk with 1 part of the salt;

(vii) admixing the temporary filtrate at step (vi) with the other ingredients at step (i) in predetermined mixing ratio to create a homogeneous mixture; wherein admixing at temperature 20° C.-25° C.;

(viii) freezing the homogeneous mixture at step (vii) in frozen molds by using an individual quick freezer (IQF) at temperature from $-29°$ C. to $-25°$ C. to create a frozen sap of inflorescence stalk blocks;

(ix) freeze-drying the frozen sap of inflorescence stalk blocks at step (viii) at a pressure of $7.8948 \times 10^{-4} - 1.3158 \times 10^{-3}$ atm, and combine increasing the temperature from ($-29°$ C. to $-25°$ C.) to 60° C. for 48 hours; results to obtain a temporary freeze-dried nipa palm powder;

(x) checking if the temporary freeze-dried nipa palm powder at step (ix) is defective or not;

if the temporary freeze-dried nipa palm powder at step (ix) has at least one of the following characteristics including: crumbled and dusty, recrystallization (crystallized water separately), and moisture content is not less than 4%, then do step (xi);

otherwise, if the temporary freeze-dried nipa palm powder at step (ix) does not have said characteristics, then to obtain a freeze-dried nipa palm powder; and (xi) grinding the freeze-dried nipa palm powder has at least one of said characteristics at step (x) to obtain a recycling mixture;

wherein the recycling mixture is reused by mixing with the temporary filtrate, and then do step (vii);

wherein a mixing ratio between the temporary filtrate and the recycling mixture is (96-99): (1-4).

These and other advantages of the present invention will no doubt become obvious to those of ordinary skill in the art after having read the following detailed description of the preferred embodiments, which are illustrated in the various drawing FIGURES.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

According to the embodiment of the present invention, a freeze-dried nipa palm powder 100 ("powder 100"). Powder 100 obtainted by mixing (75-100) part of a sap of inflorescence stalk with (0-25) part other ingredients, then freezing said sap of inflorescence stalk with said other ingredients in frozen molds using an individual quick freezer (IQF) at temperature from −25° C. to −29° C. to obtain frozen sap of inflorescence stalk blocks, and freeze drying frozen sap of inflorescence stalk molds at a pressure of $7.8948 \times 10^{-4}$–$1.3158 \times 10^{-3}$ atm for 48 hours.

According to the embodiment of the present invention, the sap of inflorescence stalk having a pH of 6-7, which has been filtered to remove impurities, has been heat treated, and has been added a salt (NaCl) at the rate of (1000-1500) of the sap of inflorescence stalk with 1 part of the salt.

According to the embodiment of the present invention, the sap of inflorescence stalk is obtained by performed in a specific order from (a') to (c') comprising: (a') choosing Nipa palm trees (*Nypa fruticans* Wurmb.) having 5 years old or more, and cleaning around the Nipa palm trees;

monitoring the Nipa palm trees after flowering for 4-5 weeks, then cutting a slice of the head of a inflorescence stalk thick 1-2 mm; wherein said cut position of the head of the inflorescence stalk forms is an inclined plane with an angle of 30°-45°;

using PE bags (Polyethylene plastic bags) to cover the position of the head of the said cut the inflorescence stalk;

(b') mechanical impacting on the inflorescence stalk (a') in the order of steps from (A) to (C) includes:

(A) appling a coffee grounds solution evenly on the inflorescence stalk, and bending the inflorescence stalk 5 times in the same direction; wherein the coffee grounds solution is obtained by dissolving a ratio of a coffee grounds having moisture content less than 18% and water having 1: (2-3);

(B) knocking the inflorescence stalk by a part wooden slats covered with cloth; wherein the wooden slats covered with cloth having the following characteristics: 35 cm long, 3.5 cm wide, 1.5 cm thick, and ½ the length of the wooden slats is covered by a 1 cm thick cloth;

knocking evenly with light force in the direction perpendicular to a surface of the inflorescence stalk, and combining translational movement of knocking along the inflorescence stalk; wherein the surface of the inflorescence stalk includes an upper surface of the inflorescence stalk, a lower surface of the inflorescence stalk, an inner surface of the inflorescence stalk, and an outer surface of the inflorescence stalk; and wherein a time of knocking time for each inflorescence stalk is 1 min;

(C) rubbing/clawing the inflorescence stalk by the palm and fingers of hands with light force, and combining translational movement rubbing/clawing along the inflorescence stalk for 1 min; wherein the hands are covered by gloves; wherein performing steps from (A) to (C) at the frequency of 1 time/day until the inflorescence stalk starts to sap, then move to step (c');

(c') collecting the sap of inflorescence stalk by following the steps from (A') to (E') including:

(A') opening the PE bags containing the sap of inflorescence stalk from the head of the inflorescence stalk, and sealing a mouth of the PE bags, then storing in container containing gel ice packs in the ratio of 1 part the gel ice packs to (3-5) parts the PE bags containing the sap of inflorescence stalk;

wherein the maximum storage time is 12 hours;

wherein the gel ice pack has been frozen for at least 8 hours;

(B') cutting a slice of the inflorescence stalk having thick 1-2 mm at the head position of the inflorescence stalk that turned brown, then using the PE bags to cover to the position of the head of the said cut the inflorescence stalk; wherein said cut position of the head of the inflorescence stalk forms is an inclined plane with an angle of 30°-45°;

(C') appling a coffee grounds solution evenly on the inflorescence stalk, and bending the inflorescence stalk 5 times in the same direction; wherein the coffee grounds solution is obtained by dissolving a ratio of a coffee grounds having moisture content less than 18% and water having 1: (2-3);

(D') knocking the inflorescence stalk by a part wooden slats covered with cloth; wherein the wooden slats covered with cloth having the following characteristics: 35 cm long, 3.5 cm wide, 1.5 cm thick, and ½ the length of the wooden slats is covered by a 1 cm thick cloth;

knocking evenly with light force in the direction perpendicular to a surface of the inflorescence stalk, and combining translational movement of knocking along the inflorescence stalk; wherein the surface of the inflorescence stalk includes an upper surface of the inflorescence stalk, a lower surface of the inflorescence stalk, an inner surface of the inflorescence stalk, and an outer surface of the inflorescence stalk; and wherein a time of knocking time for each inflorescence stalk is 1 min;

(E') rubbing/clawing the inflorescence stalk by the palm and fingers of hands with light force, and combining translational movement rubbing/clawing along the inflorescence stalk for 1 min; wherein the hands are covered by gloves;

wherein the collecting the sap of inflorescence stalk is selected from one of following at the frequency: 2 times/day, 3 times/day, and 4 times/day;

wherein each time of collecting the sap of inflorescence stalk are repeated in order from (A') to (E'), and the total time to collect the sap of inflorescence stalk in each inflorescence stalk is 30 days.

In an aspect of the present invention, using coffee grounds solution applied to the inflorescence stalk at step (A) in order to prevent insects, especially ants entering the PE bag containing the sap of the inflorescence stalk.

In an aspect of the present invention, the frequency of the collecting the sap of inflorescence stalk is 02 times/day including the first time of collecting at 5:30 am, and the second time at 4:30 pm;

wherein at the first time adding 0.2 g of sodium metabisulfite ($Na_2S_2O_5$) into the PE bags before used the PE bags to cover the position of the head of the said cut the inflorescence stalk; and wherein at the second time adding 0.25 g of sodium metabisulfite ($Na_2S_2O_5$) into the PE bags before used the PE bags to cover the position of the head of the said cut the inflorescence stalk.

According to the embodiment of the present invention, the frequency of the collecting the sap of inflorescence stalk is 03 times/day including the first time of collecting at 5:30 am, the second time at 10:30 am, and the third time at 4:30 pm; wherein at the first time and the second time, adding 0 g of sodium metabisulfite ($Na_2S_2O_5$) into the PE bags before used the PE bags to cover the position of the head of the said cut the inflorescence stalk; and wherein at the third time adding 0.25 g of sodium metabisulfite ($Na_2S_2O_5$) into the PE bags before used the PE bags to cover the position of the head of the said cut the inflorescence stalk.

According to the embodiment of the present invention, the frequency of the collecting the sap of inflorescence stalk is 04 times/day including the first time of collecting at 5:30 am, the second time at 9:30 am, the third time at 1:30 pm, and the fourth time at 4:30 pm;

wherein at the first time, the second time, and the third time adding 0 g of sodium metabisulfite ($Na_2S_2O_5$) into the PE bags before used the PE bags to cover the position of the head of the said cut the inflorescence stalk; and wherein at the fourth time adding 0.25 g of sodium metabisulfite ($Na_2S_2O_5$) into the PE bags before used the PE bags to cover the position of the head of the said cut the inflorescence stalk.

According to the preferred embodiment of the present invention, the collecting the sap of inflorescence stalk preferably at the frequency 4 times/day.

According to the embodiment of the present invention, the time cutting the slice of the inflorescence stalk having thick 1-2 mm at the head position of the inflorescence stalk that turned brown at step (B') is depended on the frequency of the collecting the sap of inflorescence stalk, including:

if the frequency of the collecting the sap of inflorescence stalk is 02 times/day that a number of times cutting the slice of the inflorescence stalk that turned brown at step (B') is two of times at two times of collecting the sap of inflorescence stalk;

if the frequency of the collecting the sap of inflorescence stalk is 03 times/day that a number of times cutting the slice of the inflorescence stalk that turned brown at step (B') is two of times at two times of collecting the sap of inflorescence stalk; wherein two times of collecting the sap of inflorescence stalk including a first time of collecting, and a third time of collecting; and if the frequency of the collecting the sap of inflorescence stalk is 04 times/day that a number of times cutting the slice of the inflorescence stalk that turned brown at step (B') is two of times at two times of collecting the sap of inflorescence stalk; wherein two times of collecting the sap of inflorescence stalk including a first time of collecting, and a fourth time of collecting.

According to the embodiment of the present invention, the other ingredients selected from the one or more of the following: a fruit ingredient, a ginger ingredient, a probiotic ingredient, and a combination thereof.

According to the preferred embodiment of the present invention, the fruit ingredient selected from the one of the fruits including: strawberries, mangoes, citrus fruits, and Indian jujubes, all listed in Table 2 below; wherein said citrus fruits including grapefruit, kumquat, lemon, lime, and orange.

TABLE 2

The fruits ingredients according to the embodiment of the present invention

| Fruits | Scientific name | Degree Brix | | | |
| --- | --- | --- | --- | --- | --- |
| | | Low | Medium | Hight | Good |
| Indian jujube | *Ziziphus mauritiana* L. | 6 | 10 | 14 | 18 |
| Grapefruit | *Citrus maxima*, *Citrus grandis* L. | 6 | 10 | 14 | 18 |
| Mango | *Mangifera indica* L. | 4 | 6 | 10 | 14 |
| Strawberry | *Fragaria vesca* L. | 6 | 10 | 12 | 14 |
| Kumquat | *Fortunella japonica* (Thunb.) Swingle, *Citrus japonica* Thunb. | 4 | 6 | 8 | 10 |
| Yellow lemon (lime) | *Citrus limon* (L.) Burm.f. - *Citrus medica* ssp. lomon L. | 4 | 6 | 8 | 10 |
| Green lemon (lemon) | *Citrus aurantifolia* | 4 | 6 | 8 | 12 |
| Oranges | *Citrus sinensis* (L.) Osheck (*C. aurantium* L. var. *dulcis* L.) | 6 | 10 | 16 | 20 |

According to the preferred embodiment of the present invention, the fruit ingredient obtained by performed in a specific order comprising:
  selecting and preparing fruits by a predetermined quality guideline, includes selecting said fruits that have a Brix level of at least 10, performing visual inspection to select ripe, which having heavy-handed, and undamaged fruits;
  washing fruits, then taking the flesh of the fruits, and removing the fruits by-products;
  squeezing the flesh of the fruits to obtained a fruits juice; and
  adjusting the Brix of the fruit juice to 15%-30% to obtained the fruit ingredient.

According to the embodiment of the present invention, the ginger ingredient obtained by performed in a specific order comprising:
  selecting and preparing ginger (*Zingiber purpureum* Roscoe.) by a predetermined quality guideline, includes:
    ginger obtained from ginger plants multiplicated by plant tissue culture technology; wherein at the budding stage using a suitable medium for in vitro multiplication of ginger shots includes: MS mineral, 30 g/L sucrose, 6.5 g/L agar, 1.5 mg/L BAP (6-Benzyl amino purine), 0.5 mg/L NAA (1-naphthalene acetic acid), and 150-200 ml/L of the sap of inflorescence stalk having a pH of 6-7;
    hard ginger, has a characteristic aroma, is not moldy, does not germinate, is not damaged, does not have the bite of worms and insects;
  squeezing ginger obtained a ginger residue;
  puring the ginger residue; and
  adjusting the humidity of the ginger residue reaches 20%-25%.

According to the embodiment of the present invention, the probiotic ingredient comprising *Lactobacillus, Streptococcus*, and *Bifidobacterium*, all listed in Table 3 below.

TABLE 3

The probiotics ingredients according to the embodiment of the invention

| Genus | Type species | Identifiers |
|---|---|---|
| *Lactobacillus* | *Lactobacillus acidophilus* | AB725355.1 |
| | *Lactobacillus acidophilus* | MN173898.1 |
| | *Lactobacillus acidophilus* | AB755424.1 |
| *Streptococcus* | *Streptococcus* sp. M40 | AB262667.1 |
| | *Streptococcus* sp. M62 | AB262658.1 |
| *Bifidobacterium* | *Bifidobacterium bifidum* | MZ596306.1 |
| | *Bifidobacterium pseudocatenulatum* | MW073427.1 |

According to the preferred embodiment of the present invention, *Lactobacillus* selected from the one or more of the species including *Lactobacillus acidophilus* (the identifier on the gene bank is AB725355.1), *Lactobacillus acidophilus* (the identifier on the gene bank is MN173898.1), *Lactobacillus acidophilus* (the identifier on the gene bank is AB755424.1), and a combination thereof.

According to the preferred embodiment of the present invention, *Streptococcus* selected from the one or more of the species including *Streptococcus* sp. M40 (the identifier on the gene bank is AB262667.1), and *Streptococcus* sp. M62 (the identifier on the gene bank is AB262658.1), and a combination thereof.

According to the preferred embodiment of the present invention, *Bifidobacterium* selected from the one or more of the species including *Bifidobacterium bifidum* (the identifier on the gene bank is MZ596306.1), and *Bifidobacterium pseudocatenulatum* (the identifier on the gene bank is MW073427.1), and a combination thereof.

According to the embodiment of the present invention, nutritional content, and immune boosting ability depend on the mixing ratio of the sap of inflorescence stalk, with the fruit ingredient, the ginger ingredient, and the probiotic ingredient, including a first formula, a second formula, a third formula, a fourth formula, and a fifth formula, all listed in Table 4 below.

According to the preferred embodiment of the present invention, the second formula is more potent than the first formula, the third formula is more potent than the second formula, the fourth formula is more potent than the third formula, and the fifth formula is more potent than the fourth formula.

According to the preferred embodiment of the present invention, the first formula comprising: 100 part of the sap of inflorescence stalk, 0 part the fruit ingredient, 0 part the ginger ingredient, and 0 part the probiotic ingredient.

According to the preferred embodiment of the present invention, the second formula comprising: (75-90) part of the sap of inflorescence stalk, (10-25) part the fruit ingredient, 0 part the ginger ingredient, and 0 part the probiotic ingredient.

According to the preferred embodiment of the present invention, the third formula comprising: (95-100) part of the sap of inflorescence stalk, 0 part the fruit ingredient, (1-5) part the ginger ingredient, and 0 part the probiotic ingredient.

According to the preferred embodiment of the present invention, the fourth formula comprising: 100 part of the sap of inflorescence stalk, 0 part the fruit ingredient, 0 part the ginger ingredient, and (0.1-0.7) part the probiotic ingredient.

TABLE 4

The mixing ingredients to create product 100 according to the five formulas of the present invention

| | Unit (w/w) | | | | |
|---|---|---|---|---|---|
| Mixing ingredients | First formula | Second formula | Third formula | Fourth formula | Fifth formula |
| Sap of inflorescence stalk | 100 | 75-90 | 95-100 | 100 | 75-90 |
| Fruits ingredients | 0 | 10-25 | 0 | 0 | 10-25 |
| Ginger | 0 | 0 | 1-5 | 0 | 0 |
| Probiotics ingredients | 0 | 0 | 0 | 0.1-0.7 | 0.1-0.7 |

Figure 1:
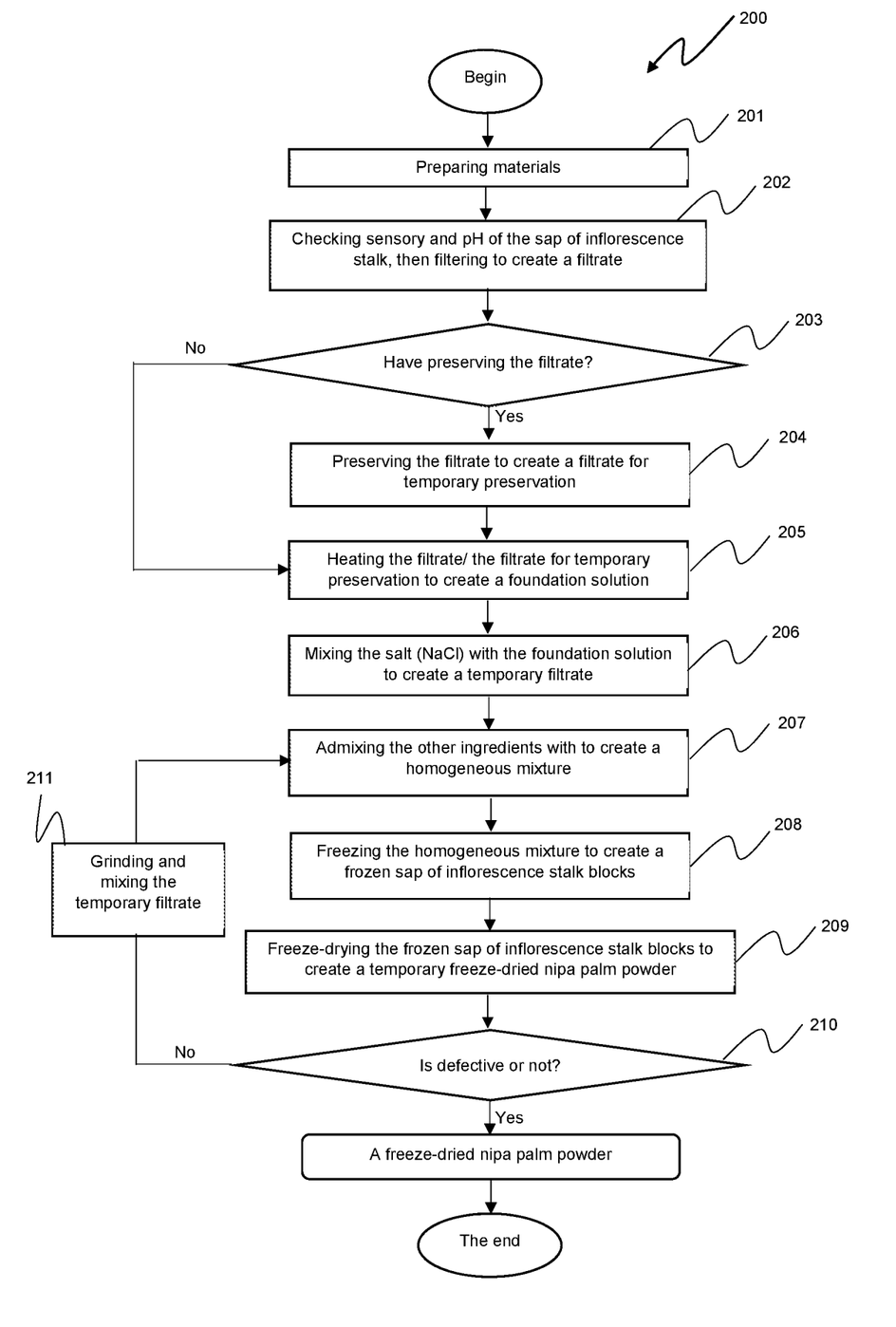
FIG. 1 is a flowchart illustrating a specific method of manufacturing the freeze-dried nipa palm powder in accordance with an exemplary embodiment of the present invention.

One embodiment of the invention is now described with reference to FIG. 1. FIG. 1 illustrating a specific method of manufacturing freeze-dried nipa palm powder ("method 200") based on the above principle in accordance with an exemplary embodiment of the present invention. In particular, method 200 is started with step 201 that preparing materials including (75-100) part of a sap of inflorescence stalk, and (0-25) part other ingredients.

According to the embodiment of the present invention, the sap of inflorescence stalk is obtained by performed in a specific order from (a') to (c') comprising:

(a') choosing Nipa palm trees (*Nypa fruticans* Wurmb.) having 5 years old or more, and cleaning around the Nipa palm trees;

monitoring the Nipa palm trees after flowering for 4-5 weeks, then cutting a slice of the head of a inflorescence stalk thick 1-2 mm; wherein said cut position of the head of the inflorescence stalk forms is an inclined plane with an angle of 30°-45°;

using PE bags (Polyethylene plastic bags) to cover the position of the head of the said cut the inflorescence stalk;

(b') mechanical impacting on the inflorescence stalk (a') in the order of steps from (A) to (C) includes:

(A) appling a coffee grounds solution evenly on the inflorescence stalk, and bending the inflorescence stalk 5 times in the same direction; wherein the coffee grounds solution is obtained by dissolving a ratio of a coffee grounds having moisture content less than 18% and water having 1: (2-3);

(B) knocking the inflorescence stalk by a part wooden slats covered with cloth; wherein the wooden slats covered with cloth having the following characteristics: 35 cm long, 3.5 cm wide, 1.5 cm thick, and ½ the length of the wooden slats is covered by a 1 cm thick cloth;

knocking evenly with light force in the direction perpendicular to a surface of the inflorescence stalk, and combining translational movement of knocking along the inflorescence stalk; wherein the surface of the inflorescence stalk includes an upper surface of the inflorescence stalk, a lower surface of the inflorescence stalk, an inner surface of the inflorescence stalk, and an outer surface of the inflorescence stalk; and wherein a time of knocking time for each inflorescence stalk is 1 min;

(C) rubbing/clawing the inflorescence stalk by the palm and fingers of hands with light force, and combining translational movement rubbing/clawing along the inflorescence stalk for 1 min; wherein the hands are covered by gloves;

wherein performing steps from (A) to (C) at the frequency of 1 time/day until the inflorescence stalk starts to sap, then move to step (c');

(c') collecting the sap of inflorescence stalk by following the steps from (A') to (E') including:

(A') opening the PE bags containing the sap of inflorescence stalk from the head of the inflorescence stalk, and sealing a mouth of the PE bags, then storing in container containing gel ice packs in the ratio of 1 part the gel ice packs to (3-5) parts the PE bags containing the sap of inflorescence stalk;

wherein the maximum storage time is 12 hours;

wherein the gel ice pack has been frozen for at least 8 hours;

(B') cutting a slice of the inflorescence stalk having thick 1-2 mm at the head position of the inflorescence stalk that turned brown, then using the PE bags to cover to the position of the head of the said cut the inflorescence stalk; wherein said cut position of the head of the inflorescence stalk forms is an inclined plane with an angle of 30°-45°;

(C') appling a coffee grounds solution evenly on the inflorescence stalk, and bending the inflorescence stalk 5 times in the same direction; wherein the coffee grounds solution is obtained by dissolving a ratio of a coffee grounds having moisture content less than 18% and water having 1: (2-3);

(D') knocking the inflorescence stalk by a part wooden slats covered with cloth; wherein the wooden slats covered with cloth having the following characteristics: 35 cm long, 3.5 cm wide, 1.5 cm thick, and ½ the length of the wooden slats is covered by a 1 cm thick cloth;

knocking evenly with light force in the direction perpendicular to a surface of the inflorescence stalk, and combining translational movement of knocking along the inflorescence stalk; wherein the surface of the inflorescence stalk includes an upper surface of the inflorescence stalk, a lower surface of the inflorescence stalk, an inner surface of the inflorescence stalk, and an outer surface of the inflorescence stalk; and wherein a time of knocking time for each inflorescence stalk is 1 min;

(E') rubbing/clawing the inflorescence stalk by the palm and fingers of hands with light force, and combining translational movement rubbing/clawing along the inflorescence stalk for 1 min; wherein the hands are covered by gloves;

wherein the collecting the sap of inflorescence stalk is selected from one of following at the frequency: 2 times/day, 3 times/day, and 4 times/day;

wherein each time of collecting the sap of inflorescence stalk are repeated in order from (A') to (E'), and the total time to collect the sap of inflorescence stalk in each inflorescence stalk is 30 days.

In an aspect of the present invention, the frequency of the collecting the sap of inflorescence stalk is 02 times/day including the first time of collecting at 5:30 am, and the second time at 4:30 pm;

wherein at the first time adding 0.2 g of sodium metabisulfite ($Na_2S_2O_5$) into the PE bags before used the PE bags to cover the position of the head of the said cut the inflorescence stalk; and wherein at the second time adding 0.25 g of sodium metabisulfite ($Na_2S_2O_5$) into the PE bags before used the PE bags to cover the position of the head of the said cut the inflorescence stalk.

According to the embodiment of the present invention, the frequency of the collecting the sap of inflorescence stalk is 03 times/day including the first time of collecting at 5:30 am, the second time at 10:30 am, and the third time at 4:30 pm;

wherein at the first time and the second time, adding 0 g of sodium metabisulfite ($Na_2S_2O_5$) into the PE bags before used the PE bags to cover the position of the head of the said cut the inflorescence stalk; and wherein at the third time adding 0.25 g of sodium metabisulfite ($Na_2S_2O_5$) into the PE bags before used the PE bags to cover the position of the head of the said cut the inflorescence stalk.

According to the embodiment of the present invention, the frequency of the collecting the sap of inflorescence stalk is 04 times/day including the first time of collecting at 5:30 am, the second time at 9:30 am, the third time at 1:30 pm, and the fourth time at 4:30 pm;

wherein at the first time, the second time, and the third time adding 0 g of sodium metabisulfite ($Na_2S_2O_5$) into the PE bags before used the PE bags to cover the position of the head of the said cut the inflorescence stalk; and wherein at the fourth time adding 0.25 g of sodium metabisulfite ($Na_2S_2O_5$) into the PE bags before used the PE bags to cover the position of the head of the said cut the inflorescence stalk.

According to the preferred embodiment of the present invention, the collecting the sap of inflorescence stalk preferably at the frequency 4 times/day.

According to the embodiment of the present invention, the time cutting the slice of the inflorescence stalk having thick 1-2 mm at the head position of the inflorescence stalk that turned brown at step (B') is depended on the frequency of the collecting the sap of inflorescence stalk, including:

if the frequency of the collecting the sap of inflorescence stalk is 02 times/day that a number of times cutting the slice of the inflorescence stalk that turned brown at step (B') is two of times at two times of collecting the sap of inflorescence stalk;

if the frequency of the collecting the sap of inflorescence stalk is 03 times/day that a number of times cutting the slice of the inflorescence stalk that turned brown at step (B') is two of times at two times of collecting the sap of inflorescence stalk; wherein two times of collecting the sap of inflorescence stalk including a first time of collecting, and a third time of collecting; and if the frequency of the collecting the sap of inflorescence stalk is 04 times/day that a number of times cutting the slice of the inflorescence stalk that turned brown at step (B') is two of times at two times of collecting the sap of inflorescence stalk; wherein two times of collecting the sap of inflorescence stalk including a first time of collecting, and a fourth time of collecting.

According to the embodiment of the present invention, the other ingredients selected from the one or more of the following: a fruit ingredient, a ginger ingredient, a probiotic ingredient, and a combination thereof.

According to the preferred embodiment of the present invention, the fruit ingredient selected from the one of the fruits including: strawberries (*Fragaria vesca* L.), mangoes (*Mangifera indica* L.), citrus fruits, and Indian jujubes (*Ziziphus mauritiana* L.); wherein said citrus fruits including grapefruit (*Citrus maxima, Citrus grandis* L.), kumquat (*Fortunella japonica* (Thunb.) Swingle, *Citrus japonica* Thunb.), lemon (*Citrus aurantifolia*), lime (*Citrus limon* (L.) Burm.f.—*Citrus medica* ssp. lomon L.), and orange (*Citrus sinensis* (L.) Osheck (*C. aurantium* L. var. *dulcis* L.).

According to the preferred embodiment of the present invention, the fruit ingredient obtained by performed in a specific order comprising:

selecting and preparing fruits by a predetermined quality guideline, includes selecting said fruits that have a Brix level of at least 10, performing visual inspection to select ripe, which having heavy-handed, and undamaged fruits;

washing fruits, then taking the flesh of the fruits, and removing the fruits by-products;

squeezing the flesh of the fruits to obtained a fruits juice; and adjusting the Brix of the fruit juice to 15%-30% to obtained the fruit ingredient.

According to the embodiment of the present invention, the ginger ingredient obtained by performed in a specific order comprising:

selecting and preparing ginger (*Zingiber purpureum* Roscoe.) by a predetermined quality guideline, includes ginger obtained from ginger plants multiplicated by plant tissue culture technology; wherein at the budding stage using a suitable medium for in vitro multiplication of ginger shots includes: MS mineral, 30 g/L sucrose, 6.5 g/L agar, 1.5 mg/L BAP (6-Benzyl amino purine), 0.5 mg/L NAA (1-naphthalene acetic acid), and 150-200 ml/L of the sap of inflorescence stalk having a pH of 6-7;

hard ginger, has a characteristic aroma, is not moldy, does not germinate, is not damaged, does not have the bite of worms and insects;

squeezing ginger obtained a ginger residue;

puring the ginger residue; and adjusting the humidity of the ginger residue reaches 20%-25%.

According to the embodiment of the present invention, the probiotic ingredient comprising *Lactobacillus, Streptococcus*, and *Bifidobacterium*, all listed in Table 3.

According to the preferred embodiment of the present invention, *Lactobacillus* selected from the one or more of the species including *Lactobacillus acidophilus* (the identifier on the gene bank is AB725355.1), *Lactobacillus acidophilus* (the identifier on the gene bank is MN173898.1), *Lactobacillus acidophilus* (the identifier on the gene bank is AB755424.1), and a combination thereof.

According to the preferred embodiment of the present invention, *Streptococcus* selected from the one or more of the species including *Streptococcus* sp. M40 (the identifier on the gene bank is AB262667.1), and *Streptococcus* sp. M62 (the identifier on the gene bank is AB262658.1), and a combination thereof.

According to the preferred embodiment of the present invention, *Bifidobacterium* selected from the one or more of the species including *Bifidobacterium bifidum* (the identifier on the gene bank is MZ596306.1), and *Bifidobacterium pseudocatenulatum* (the identifier on the gene bank is MW073427.1), and a combination thereof.

Within the scope of the present invention, the term "probiotic ingredient" obtained by increasing the biomass from said probiotic bacteria. The term "probiotic ingredient" is also understood as the product obtained by centrifugation of the biomass from the fermentation of probiotic with said identification code on the gene bank. However, it is not limited to, for example, the "probiotic ingredient" obtained by the above method that are further processed using other methods such as microencapsulation of probiotics by spray drying, microencapsulation of probiotics by lyophilization, or a combination, are also included in the term "probiotic ingredient" according in the embodiment of the present invention, as long as the minimum density probiotic is maintained during storage greater than $10^7$ CFU/g.

At step 202, checking sensory and pH of the sap of inflorescence stalk; if the sap of inflorescence stalk at step 201 has the following characteristics including: aroma of young and sweet nipa palm meat, no coagulation, the sap is clear yellow, and pH is 6-7; then filtering the sap of inflorescence stalk at step 201 to create a filtrate by a sieve with a pore size of 0.045 mm. Otherwise, the sap of inflorescence stalk at step (i) does not have the said characteristics, it shall be removed.

At step 203, considering whether to preserve the filtrate at step 202. If the filtrate at step 202 does not need to to be processed immediately, then do step 204; otherwise, if the filtrate at step 202 needs to be processed immediately, then do step 205.

At step 204, preserving the filtrate at step 202 by selecting one of two following option preserves depending on the time preservation, including: a first option, and a second option. According to the embodiment of the invention, preservation of the filtrate at step 202 according to the first option at 2-4° C. for 3 days. Preservation of the filtrate at step 202 according to the second option at −18° C. for 6 months. The result obtained at step 204 is a filtrate for temporary preservation.

At step 205, heating the filtrate at step 202/the filtrate for temporary preservation at step 205 at 20° C. to create a foundation solution.

At step 206, mixing a salt (NaCl) with the foundation solution at step 205 to create a temporary filtrate. According to the preferred embodiment of the invention, the salt is added according to the ratio of 1 part corresponding with salt (1000-1500) part of the sap of inflorescence stalk.

At step 207, admixing the other ingredients at step 201 with the temporary filtrate at step 206 in predetermined mixing ratio to create a homogeneous mixture; wherein admixing at temperature 20° C.-25° C.

Within the scope of the present invention, the term "homogeneous mixture" includes the following meanings:

(a) A homogeneous mixture is a solution that completely dissolves the foundation solution with the salt (NaCl); wherein the admixing ratio is (1000-1500) part of the sap of inflorescence stalk with 1 part of the salt;

(b) A homogeneous mixture is a solution that acts as a reactant allowing the addition of the other ingredients to contribute their chemical and physical properties to create a new preparation; and (c) A homogeneous mixture is a solution chemically bonds with the fruit ingredient, the ginger ingredient, and the probiotic ingredient such as ionization reactions, covalent reactions, reducing reactions, replacement reactions, and rearrangement reactions to form a new chemical composition.

It should be noted that the term "admixed/mixed/admixing/mixing" as used in the present invention is understood to mean adding, or reacting, or dissolving homogeneously, or evenly, components in the same solution/mixture. Step 207 is performed by a magnetic stirrer. Magnetic stirrer has been known in previous art so the description of the structure and its operating principle will not be described in detail in the invention.

According to the preferred embodiment of the invention, the homogeneous mixture at step 207 comprising: 100 part of the sap of inflorescence stalk, 0 part the fruit ingredient, 0 part the ginger ingredient, and 0 part the probiotic ingredient.

According to the preferred embodiment of the invention, the homogeneous mixture at step 207 comprising: (75-90) part of the sap of inflorescence stalk, (10-25) part the fruit ingredient, 0 part the ginger ingredient, and 0 part the probiotic ingredient.

According to the preferred embodiment of the invention, the homogeneous mixture at step 207 comprising: (95-100)

part of the sap of inflorescence stalk, 0 part the fruit ingredient, (1-5) part the ginger ingredient, and 0 part the probiotic ingredient.

According to the preferred embodiment of the invention, the homogeneous mixture at step 207 comprising: 100 part of the sap of inflorescence stalk, 0 part the fruit ingredient, 0 part the ginger ingredient, and (0.1-0.7) part the probiotic ingredient.

According to the preferred embodiment of the invention, the homogeneous mixture at step 207 comprising: (75-90) part of the sap of inflorescence stalk, (10-25) part the fruit ingredient, 0 part the ginger ingredient, and (0.1-0.7) part the probiotic ingredient.

At step 208, freezing the homogeneous mixture at step 207 in frozen molds by using an individual quick freezer (IQF) at temperature from −29° C. to −25° C. to create a frozen sap of inflorescence stalk blocks. Step 208 is performed by the individual quick freezer (IQF). The individual quick freezer (IQF) has been known in previous art so the description of the structure and its operating principle will not be described in detail in the invention.

At step 209, freeze-drying the frozen sap of inflorescence stalk blocks at step 208 at a pressure of $7.8948 \times 10^{-4}$ – $1.3158 \times 10^{-3}$ atm, and combine increasing the temperature from (−29° C. to −25° C.) to 60° C. for 48 hours; results to obtain a temporary freeze-dried nipa palm powder.

At step 210, checking if the temporary freeze-dried nipa palm powder at step 209 is defective or not;

if the temporary freeze-dried nipa palm powder at step 209 has at least one of the following characteristics including: crumbled and dusty, recrystallization (crystallized water separately), and moisture content is not less than 4%, then do step 211;

otherwise, if the temporary freeze-dried nipa palm powder at step 209 does not have said characteristics, then to obtain a freeze-dried nipa palm powder (is the powder 100).

Finally, at step 211 grinding the freeze-dried nipa palm powder has at least one of the following said characteristics at step 210 to obtain a recycling mixture. According to the embodiment of the invention, the recycling mixture is reused by mixing with the temporary filtrate at step 206, and then do step 207.

According to the preferred embodiment of the invention, a mixing ratio between the temporary filtrate and the recycling mixture is (96-99): (1-4).

According to the embodiment of the invention, the powder 100 obtained from the method 200 is used as a beverage, a functional food to supplement nutritional sources and strengthen the body's resistance.

The purpose of the following examples is to demonstrate that the technical solution of this invention has been successfully researched and tested by the author. Specifically, the production method 200 produces 200 Kg of the powder 100 according to embodiments of the present invention.

The powder 100 including 08 options (eight options) according to the first formula, and the second formula; all options listed Table 5 below.

TABLE 5

Experimental embodiments of the powder 100 according to the first formula and second formula are taken as examples of the present invention

| | | Options | | | | | | | |
|---|---|---|---|---|---|---|---|---|---|
| Ingredients | | 1 | 2 | 3 | 4 | 5 | 6 | 7 | 8 |
| Sap of inflorescence stalk (L) | | 100 | 75-90 | 75-90 | 75-90 | 75-90 | 75-90 | 75-90 | 75-90 |
| Fruits ingredients (L) | Strawberry | 0 | 10-25 | 0 | 0 | 0 | 0 | 0 | 0 |
| | Mango | 0 | 0 | 10-25 | 0 | 0 | 0 | 0 | 0 |
| | Indian jujube | 0 | 0 | 0 | 10-25 | 0 | 0 | 0 | 0 |
| | Grapefruit | 0 | 0 | 0 | 0 | 10-25 | 0 | 0 | 0 |
| | Kumquat | 0 | 0 | 0 | 0 | 0 | 10-25 | 0 | 0 |
| | Yellow lemon (lime) | 0 | 0 | 0 | 0 | 0 | 0 | 10-25 | 0 |
| | Green lemon (lemon) | 0 | 0 | 0 | 0 | 0 | 0 | 0 | 10-25 |
| Ginger (Kg) | | 0 | 0 | 0 | 0 | 0 | 0 | 0 | 0 |
| Probiotics ingredients (Kg) | | 0 | 0 | 0 | 0 | 0 | 0 | 0 | 0 |

The powder 100 including 09 options (nine options) according to the third formula; all options listed Table 6 below.

TABLE 6

Experimental embodiments of the powder 100 according to the third formula are taken as examples of the present invention

| | Options | | | | | | | | |
|---|---|---|---|---|---|---|---|---|---|
| Ingredients | 9 | 10 | 11 | 12 | 13 | 14 | 15 | 16 | 17 |
| Sap of inflorescence stalk (L) | 95 | 95.5 | 96 | 96.5 | 97 | 97.9 | 98 | 98.5 | 99 |
| Fruits ingredients (L) | 0 | 0 | 0 | 0 | 0 | 0 | 0 | 0 | 0 |
| Ginger (kg) | 5 | 4.5 | 4 | 3.5 | 3 | 2.5 | 2 | 1.5 | 1 |
| Probiotics ingredients (kg) | 0 | 0 | 0 | 0 | 0 | 0 | 0 | 0 | 0 |

The powder 100 including 62 options (sixty two options) according to the fourth formula; all options listed Table 7 below.

TABLE 7

Experimental embodiments of the powder 100 according to the fourth formula are taken as examples of the present invention

| Options | Sap of inflorescence stalk (L) | Fruits ingredients (L) | Ginger (kg) | Probiotics ingredients (kg) | | | | | | |
|---|---|---|---|---|---|---|---|---|---|---|
| | | | | I | II | III | IV | V | VI | VII |
| 18 | 100 | 0 | 0 | 0.1 | 0.1 | 0.1 | 0.1 | 0.1 | 0.1 | 0.1 |
| 19 | 100 | 0 | 0 | 0 | 0.1 | 0.1 | 0.1 | 0.1 | 0.1 | 0.1 |
| 20 | 100 | 0 | 0 | 0.1 | 0 | 0.1 | 0.1 | 0.1 | 0.1 | 0.1 |
| 21 | 100 | 0 | 0 | 0.1 | 0.1 | 0 | 0.1 | 0.1 | 0.1 | 0.1 |
| 22 | 100 | 0 | 0 | 0.1 | 0.1 | 0.1 | 0.1 | 0.1 | 0.1 | 0 |

TABLE 7-continued

Experimental embodiments of the powder 100 according to the fourth formula are taken as examples of the present invention

| Options | Sap of inflorescence stalk (L) | Fruits ingredients (L) | Ginger (kg) | Probiotics ingredients (kg) | | | | | | |
|---|---|---|---|---|---|---|---|---|---|---|
| | | | | I | II | III | IV | V | VI | VII |
| 23 | 100 | 0 | 0 | 0.1 | 0.1 | 0.1 | 0.1 | 0.1 | 0 | 0.1 |
| 24 | 100 | 0 | 0 | 0.1 | 0.1 | 0.1 | 0.1 | 0 | 0.1 | 0.1 |
| 25 | 100 | 0 | 0 | 0.1 | 0.1 | 0.1 | 0 | 0.1 | 0.1 | 0.1 |
| 26 | 100 | 0 | 0 | 0.1 | 0.1 | 0.1 | 0.1 | 0 | 0.1 | 0 |
| 27 | 100 | 0 | 0 | 0.1 | 0.1 | 0.1 | 0.1 | 0 | 0 | 0.1 |
| 28 | 100 | 0 | 0 | 0.1 | 0.1 | 0.1 | 0 | 0.1 | 0.1 | 0 |
| 29 | 100 | 0 | 0 | 0.1 | 0.1 | 0.1 | 0 | 0.1 | 0 | 0.1 |
| 30 | 100 | 0 | 0 | 0.1 | 0.1 | 0 | 0.1 | 0.1 | 0.1 | 0 |
| 31 | 100 | 0 | 0 | 0.1 | 0.1 | 0 | 0.1 | 0.1 | 0 | 0.1 |
| 32 | 100 | 0 | 0 | 0.1 | 0 | 0.1 | 0.1 | 0.1 | 0.1 | 0 |
| 33 | 100 | 0 | 0 | 0.1 | 0 | 0.1 | 0.1 | 0.1 | 0 | 0.1 |
| 34 | 100 | 0 | 0 | 0 | 0.1 | 0.1 | 0.1 | 0.1 | 0.1 | 0 |
| 35 | 100 | 0 | 0 | 0 | 0.1 | 0.1 | 0.1 | 0.1 | 0 | 0.1 |
| 36 | 100 | 0 | 0 | 0.1 | 0.1 | 0 | 0.1 | 0 | 0.1 | 0.1 |
| 37 | 100 | 0 | 0 | 0.1 | 0.1 | 0 | 0 | 0.1 | 0.1 | 0.1 |
| 38 | 100 | 0 | 0 | 0.1 | 0 | 0.1 | 0.1 | 0 | 0.1 | 0.1 |
| 39 | 100 | 0 | 0 | 0.1 | 0 | 0.1 | 0 | 0.1 | 0.1 | 0.1 |
| 40 | 100 | 0 | 0 | 0 | 0.1 | 0.1 | 0.1 | 0 | 0.1 | 0.1 |
| 41 | 100 | 0 | 0 | 0 | 0.1 | 0.1 | 0 | 0.1 | 0.1 | 0.1 |
| 42 | 100 | 0 | 0 | 0.1 | 0 | 0 | 0.1 | 0.1 | 0.1 | 0.1 |
| 43 | 100 | 0 | 0 | 0 | 0.1 | 0 | 0.1 | 0.1 | 0.1 | 0.1 |
| 44 | 100 | 0 | 0 | 0 | 0 | 0.1 | 0.1 | 0.1 | 0.1 | 0.1 |
| 45 | 100 | 0 | 0 | 0.1 | 0 | 0 | 0.1 | 0 | 0.1 | 0.1 |
| 46 | 100 | 0 | 0 | 0.1 | 0 | 0 | 0 | 0.1 | 0.1 | 0.1 |
| 47 | 100 | 0 | 0 | 0 | 0.1 | 0 | 0.1 | 0 | 0.1 | 0.1 |
| 48 | 100 | 0 | 0 | 0 | 0.1 | 0 | 0 | 0.1 | 0.1 | 0.1 |
| 49 | 100 | 0 | 0 | 0 | 0 | 0.1 | 0.1 | 0 | 0.1 | 0.1 |
| 50 | 100 | 0 | 0 | 0 | 0 | 0.1 | 0 | 0.1 | 0.1 | 0.1 |
| 51 | 100 | 0 | 0 | 0.1 | 0 | 0 | 0.1 | 0.1 | 0.1 | 0 |
| 52 | 100 | 0 | 0 | 0.1 | 0 | 0 | 0.1 | 0.1 | 0 | 0.1 |
| 53 | 100 | 0 | 0 | 0 | 0.1 | 0 | 0.1 | 0.1 | 0.1 | 0 |
| 54 | 100 | 0 | 0 | 0 | 0.1 | 0 | 0.1 | 0.1 | 0 | 0.1 |
| 55 | 100 | 0 | 0 | 0 | 0 | 0.1 | 0.1 | 0.1 | 0.1 | 0 |
| 56 | 100 | 0 | 0 | 0 | 0 | 0.1 | 0.1 | 0.1 | 0 | 0.1 |
| 57 | 100 | 0 | 0 | 0.1 | 0.1 | 0 | 0.1 | 0 | 0.1 | 0 |
| 58 | 100 | 0 | 0 | 0.1 | 0.1 | 0 | 0.1 | 0 | 0 | 0.1 |
| 59 | 100 | 0 | 0 | 0.1 | 0.1 | 0 | 0 | 0.1 | 0.1 | 0 |
| 60 | 100 | 0 | 0 | 0.1 | 0.1 | 0 | 0 | 0.1 | 0 | 0.1 |
| 61 | 100 | 0 | 0 | 0 | 0.1 | 0.1 | 0 | 0.1 | 0 | 0 |
| 62 | 100 | 0 | 0 | 0 | 0.1 | 0.1 | 0.1 | 0 | 0 | 0.1 |
| 63 | 100 | 0 | 0 | 0 | 0.1 | 0.1 | 0 | 0.1 | 0.1 | 0 |
| 64 | 100 | 0 | 0 | 0 | 0.1 | 0 | 0.1 | 0 | 0.1 | 0.1 |
| 65 | 100 | 0 | 0 | 0.1 | 0 | 0.1 | 0.1 | 0 | 0.1 | 0 |
| 66 | 100 | 0 | 0 | 0.1 | 0 | 0.1 | 0.1 | 0 | 0 | 0.1 |
| 67 | 100 | 0 | 0 | 0.1 | 0 | 0.1 | 0 | 0.1 | 0.1 | 0 |
| 68 | 100 | 0 | 0 | 0.1 | 0 | 0.1 | 0 | 0.1 | 0 | 0.1 | wherein, I is AB725355.1; II is MN173898.1; III is AB755424.1; IV is AB262667.1; V is AB262658.1; VI is MZ596306.1; and VII is MW073427.1.

The powder 100 including 51 options (sixty two options) according to the fifth formula; all options listed Table 8 below.

TABLE 8

Experimental embodiments of the powder 100 according to the fifth formula are taken as examples of the present invention

| Options | Sap of inflorescence stalk (L) | Fruits ingredients (L) | Ginger | Probiotics ingredients (Kg) | | | | | | |
|---|---|---|---|---|---|---|---|---|---|---|
| | | | | I | II | III | IV | V | VI | VII |
| 69 | 75-90 | 10-25 | 0 | | | | | | | |
| 70 | 75-90 | 10-25 | 0 | 0.1 | 0.1 | 0.1 | 0.1 | 0.1 | 0.1 | 0.1 |
| 71 | 75-90 | 10-25 | 0 | 0 | 0.1 | 0.1 | 0.1 | 0.1 | 0.1 | 0.1 |
| 72 | 75-90 | 10-25 | 0 | 0.1 | 0 | 0.1 | 0.1 | 0.1 | 0.1 | 0.1 |
| 73 | 75-90 | 10-25 | 0 | 0.1 | 0.1 | 0 | 0.1 | 0.1 | 0.1 | 0.1 |
| 74 | 75-90 | 10-25 | 0 | 0.1 | 0.1 | 0.1 | 0.1 | 0.1 | 0.1 | 0 |
| 75 | 75-90 | 10-25 | 0 | 0.1 | 0.1 | 0.1 | 0.1 | 0.1 | 0 | 0.1 |
| 76 | 75-90 | 10-25 | 0 | 0.1 | 0.1 | 0.1 | 0.1 | 0 | 0.1 | 0.1 |
| 77 | 75-90 | 10-25 | 0 | 0.1 | 0.1 | 0.1 | 0 | 0.1 | 0.1 | 0.1 |
| 78 | 75-90 | 10-25 | 0 | 0.1 | 0.1 | 0.1 | 0 | 0.1 | 0.1 | 0 |
| 79 | 75-90 | 10-25 | 0 | 0.1 | 0.1 | 0.1 | 0.1 | 0 | 0 | 0.1 |
| 80 | 75-90 | 10-25 | 0 | 0.1 | 0.1 | 0.1 | 0 | 0.1 | 0.1 | 0 |
| 81 | 75-90 | 10-25 | 0 | 0.1 | 0.1 | 0.1 | 0 | 0.1 | 0 | 0.1 |
| 82 | 75-90 | 10-25 | 0 | 0.1 | 0.1 | 0 | 0.1 | 0.1 | 0 | 0 |
| 83 | 75-90 | 10-25 | 0 | 0.1 | 0.1 | 0 | 0.1 | 0.1 | 0 | 0.1 |
| 84 | 75-90 | 10-25 | 0 | 0.1 | 0 | 0.1 | 0.1 | 0.1 | 0.1 | 0 |
| 85 | 75-90 | 10-25 | 0 | 0.1 | 0 | 0.1 | 0.1 | 0.1 | 0 | 0.1 |
| 86 | 75-90 | 10-25 | 0 | 0 | 0.1 | 0.1 | 0.1 | 0.1 | 0 | 0 |
| 87 | 75-90 | 10-25 | 0 | 0 | 0.1 | 0.1 | 0.1 | 0.1 | 0 | 0.1 |
| 88 | 75-90 | 10-25 | 0 | 0.1 | 0.1 | 0 | 0.1 | 0 | 0.1 | 0.1 |
| 89 | 75-90 | 10-25 | 0 | 0.1 | 0.1 | 0 | 0 | 0.1 | 0.1 | 0.1 |
| 90 | 75-90 | 10-25 | 0 | 0.1 | 0 | 0.1 | 0.1 | 0 | 0.1 | 0.1 |
| 91 | 75-90 | 10-25 | 0 | 0.1 | 0 | 0.1 | 0 | 0.1 | 0.1 | 0.1 |
| 92 | 75-90 | 10-25 | 0 | 0 | 0.1 | 0.1 | 0.1 | 0 | 0.1 | 0.1 |
| 93 | 75-90 | 10-25 | 0 | 0 | 0.1 | 0.1 | 0 | 0.1 | 0.1 | 0.1 |
| 94 | 75-90 | 10-25 | 0 | 0.1 | 0 | 0 | 0.1 | 0.1 | 0.1 | 0.1 |
| 95 | 75-90 | 10-25 | 0 | 0 | 0.1 | 0 | 0.1 | 0.1 | 0.1 | 0.1 |
| 96 | 75-90 | 10-25 | 0 | 0 | 0 | 0.1 | 0.1 | 0.1 | 0.1 | 0.1 |
| 97 | 75-90 | 10-25 | 0 | 0.1 | 0 | 0 | 0.1 | 0 | 0.1 | 0.1 |
| 98 | 75-90 | 10-25 | 0 | 0.1 | 0 | 0 | 0 | 0.1 | 0.1 | 0.1 |
| 99 | 75-90 | 10-25 | 0 | 0 | 0.1 | 0 | 0.1 | 0 | 0.1 | 0.1 |
| 100 | 75-90 | 10-25 | 0 | 0 | 0.1 | 0 | 0 | 0.1 | 0.1 | 0.1 |
| 101 | 75-90 | 10-25 | 0 | 0 | 0 | 0.1 | 0.1 | 0 | 0.1 | 0.1 |
| 102 | 75-90 | 10-25 | 0 | 0 | 0 | 0.1 | 0 | 0.1 | 0.1 | 0.1 |
| 103 | 75-90 | 10-25 | 0 | 0.1 | 0 | 0 | 0.1 | 0.1 | 0.1 | 0 |
| 104 | 75-90 | 10-25 | 0 | 0.1 | 0 | 0 | 0.1 | 0.1 | 0 | 0.1 |
| 105 | 75-90 | 10-25 | 0 | 0 | 0.1 | 0 | 0.1 | 0.1 | 0.1 | 0 |
| 106 | 75-90 | 10-25 | 0 | 0 | 0.1 | 0 | 0.1 | 0.1 | 0 | 0.1 |
| 107 | 75-90 | 10-25 | 0 | 0 | 0 | 0.1 | 0.1 | 0.1 | 0.1 | 0 |
| 108 | 75-90 | 10-25 | 0 | 0 | 0 | 0.1 | 0.1 | 0.1 | 0 | 0.1 |
| 109 | 75-90 | 10-25 | 0 | 0.1 | 0.1 | 0 | 0.1 | 0 | 0.1 | 0 |
| 110 | 75-90 | 10-25 | 0 | 0.1 | 0.1 | 0 | 0.1 | 0 | 0 | 0.1 |
| 111 | 75-90 | 10-25 | 0 | 0.1 | 0.1 | 0 | 0 | 0.1 | 0.1 | 0 |
| 112 | 75-90 | 10-25 | 0 | 0.1 | 0.1 | 0 | 0 | 0.1 | 0 | 0.1 |
| 113 | 75-90 | 10-25 | 0 | 0 | 0.1 | 0.1 | 0.1 | 0 | 0.1 | 0 |
| 114 | 75-90 | 10-25 | 0 | 0 | 0.1 | 0.1 | 0.1 | 0 | 0 | 0.1 |
| 115 | 75-90 | 10-25 | 0 | 0 | 0.1 | 0.1 | 0 | 0.1 | 0.1 | 0 |
| 116 | 75-90 | 10-25 | 0 | 0 | 0.1 | 0.1 | 0 | 0.1 | 0 | 0.1 |
| 117 | 75-90 | 10-25 | 0 | 0.1 | 0 | 0.1 | 0.1 | 0 | 0.1 | 0 |
| 118 | 75-90 | 10-25 | 0 | 0.1 | 0 | 0.1 | 0.1 | 0 | 0 | 0.1 |
| 119 | 75-90 | 10-25 | 0 | 0.1 | 0 | 0.1 | 0 | 0.1 | 0.1 | 0 |
| 120 | 75-90 | 10-25 | 0 | 0.1 | 0 | 0.1 | 0 | 0.1 | 0 | 0.1 | wherein, I is AB725355.1; II is MN173898.1; III is AB755424.1; IV is AB262667.1; V is AB262658.1; VI is MZ596306.1; and VII is MW073427.1.

According to some of the example listed to Tables 5-8, the powder 100 including 130 options according to the first to the fifth formula. The powder 100 is white as the main color, in addition to the color of the mixed the fruit ingredient or the color of the ginger ingredient. The powder 100 has a crunchy, spongy texture, moderate firmness, easily soluble in water, and has the characteristic odor of the sap of inflorescence stalk and mixed the fruits or ginger ingredients. The powder 100 can be used directly or diluted with water to drink.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of manufacturing a freeze-dried nipa palm powder comprising steps performed in the following specific orders:
   (i) Preparing materials including (75-100) part of a sap of inflorescence stalk, and (0-25) part other ingredients;
      wherein the other ingredients are selected from the group consisting of a fruit ingredient, a ginger ingredient, a probiotic ingredient, and a combination thereof;
      wherein the sap of inflorescence stalk is obtained by performing in a specific order from (a') to (c') comprising:
      (a') choosing Nipa palm trees 5 years old or more, and cleaning around the Nipa palm trees;
         monitoring the Nipa palm trees after flowering for 4-5 weeks, then cutting a slice of the head of a inflorescence stalk with thickness of 1-2 mm; wherein cut position of the head of the inflorescence stalk forms an inclined plane with an angle of 30°-45°;
         using PE bags (Polyethylene plastic bags) to cover the cut position of the head of the inflorescence stalk;
      (b') mechanical impacting on the inflorescence stalk (a') in the order of steps from (A) to (C) includes:
         (A) appling a coffee grounds solution evenly on the inflorescence stalk, and bending the inflorescence stalk 5 times in the same direction; wherein the coffee grounds solution is obtained by dissolving coffee grounds having moisture content less than 18% in water, with a ratio of coffee grounds to water at 1: (2-3);
         (B) knocking the inflorescence stalk by wooden slats covered with cloth; wherein the wooden slats covered with cloth having the following characteristics: 35 cm long, 3.5 cm wide, 1.5 cm thick, and half of the length of the wooden slats is covered by a 1 cm thick cloth;
         knocking evenly with light force in the direction perpendicular to a surface of the inflorescence stalk along the inflorescence stalk; wherein the surface of the inflorescence stalk includes an upper surface of the inflorescence stalk, a lower surface of the inflorescence stalk, an inner surface of the inflorescence stalk, and an outer surface of the inflorescence stalk; and wherein knocking time for each inflorescence stalk is 1 min;
         (C) rubbing/clawing the inflorescence stalk by the palm and fingers of hands with light force along the inflorescence stalk for 1 min; wherein the hands are covered by gloves;
         wherein performing steps from (A) to (C) at the frequency of 1 time/day until the inflorescence stalk starts to sap, then move to step (c');
      (c') collecting the sap of inflorescence stalk by following the steps from (A') to (E') including:
         (A') opening the PE bags containing the sap of inflorescence stalk from the head of the inflorescence stalk, and sealing a mouth of the PE bags, then storing in a container containing gel ice packs in the ratio of 1 part the gel ice packs to (3-5) parts the PE bags containing the sap of inflorescence stalk;
         wherein the maximum storage time is 12 hours;
         wherein the gel ice pack has been frozen for at least 8 hours;
         (B') cutting a slice of the inflorescence stalk with a thickness of 1-2 mm at the head position of the inflorescence stalk that turned brown, then using the PE bags to cover to the cut position of the head of the inflorescence stalk;
         wherein the form of said cut position of the head of the inflorescence stalk is an inclined plane with an angle of 30°-45°;
         (C') appling a coffee grounds solution evenly on the inflorescence stalk, and bending the inflorescence stalk 5 times in the same direction; wherein the coffee grounds solution is obtained by dissolving coffee grounds having moisture content less than 18% in water, with a ratio of coffee grounds to water at 1: (2-3);
         (D') knocking the inflorescence stalk by wooden slats covered with cloth; wherein the wooden slats covered with cloth having the following characteristics: 35 cm long, 3.5 cm wide, 1.5 cm thick, and half of the length of the wooden slats is covered by a 1 cm thick cloth;
         knocking evenly with light force in the direction perpendicular to a surface of the inflorescence stalk along the inflorescence stalk; wherein the surface of the inflorescence stalk includes an upper surface of the inflorescence stalk, a lower surface of the inflorescence stalk, an inner surface of the inflorescence stalk, and an outer surface of the inflorescence stalk; and wherein knocking time for each inflorescence stalk is 1 min;

(E') rubbing/clawing the inflorescence stalk by the palm and fingers of hands with light force along the inflorescence stalk for 1 min; wherein the hands are covered by gloves;
wherein the collecting the sap of inflorescence stalk is selected from one of following frequency: 2 times/day, 3 times/day, and 4 times/day;
wherein each time of collecting the sap of inflorescence stalk are repeated in order from (A') to (E'), and the total time to collect the sap of inflorescence stalk in each inflorescence stalk is 30 days;
wherein the fruit ingredient is selected from the group consisting of: strawberries, mangoes, Indian jujubes, grapefruit, kumquat, lemon, lime, and orange; and
wherein the fruit ingredient is obtained by performing in a specific order comprising:
selecting and preparing fruits by a predetermined quality guideline, includes
selecting said fruits that have a Brix level of at least 10, performing visual
inspection to select ripe, heavy, and undamaged fruits;
washing fruits, then taking the flesh of the fruits, and removing the fruits by-products;
squeezing the flesh of the fruits to obtain a fruits juice; and
adjusting the Brix of the fruit juice to 15%-30% to to obtain the fruit ingredient;
wherein the ginger ingredient is obtained by performing in a specific order comprising:
selecting and preparing ginger by a predetermined quality guideline, includes
ginger obtained by plant tissue culture technology; wherein at the budding stage using a suitable medium for in vitro multiplication of ginger shots includes: MS medium (Murashige and Skoog medium), 30 g/L sucrose, 6.5 g/L agar, 1.5 mg/L BAP (6-Benzyl amino purine), 0.5 mg/L NAA (1-naphthalene acetic acid), and 150-200 ml/L of the sap of inflorescence stalk having a pH of 6-7;
ginger has a characteristic aroma, is not moldy, does not germinate, is not damaged, does not have the bite of worms and insects;
squeezing ginger to obtain a ginger residue; and
adjusting the humidity of the ginger residue to reach 20%-25%;
wherein the probiotic ingredient comprising *Lactobacillus, Streptococcus*, and *Bifidobacterium*;
wherein said *Lactobacillus* is selected from the group consisting of *Lactobacillus acidophilus, Lactobacillus acidophilus, Lactobacillus acidophilus*, and a combination thereof;
wherein said *Streptococcus* is selected from the group consisting of *Streptococcus* sp. M40, *Streptococcus* sp. M62, and a combination thereof;
wherein said *Bifidobacterium* is selected from the group consisting of *Bifidobacterium bifidum, Bifidobacterium pseudocatenulatum*, and a combination thereof;
(ii) checking sensory and pH of the sap of inflorescence stalk;
if the sap of inflorescence stalk at step (i) has the following characteristics including: the sap is clear yellow, and pH is 6-7, then filtering the sap of inflorescence stalk at step (i) to create a filtrate by a sieve with a pore size of 0.045 mm;
otherwise, the sap of inflorescence stalk at step (i) shall be removed;
(iii) considering whether to preserve the filtrate at step (ii);
if the filtrate at step (ii) does not need to to be processed immediately, then do step (iv);
otherwise, if the filtrate at step (ii) needs to be processed immediately, then do step (v);
(iv) preserving the filtrate at step (ii) by selecting one of two following preservation options depending on the time preservation, including:
a first option: preserving the filtrate at step (ii) at 2-4° C. for 3 days; and
a second option: preserving the filtrate at step (ii) at −18° C. for 6 months;
the result obtained at step (iv) is a filtrate for temporary preservation;
(v) heating the filtrate at step (ii)/the filtrate for temporary preservation at step (iv) at 20° C. to create a foundation solution;
(vi) mixing a salt with the foundation solution at step (v) to create a temporary filtrate;
wherein a mixing ratio is (1000-1500) part of the sap of inflorescence stalk with 1 part of the salt;
(vii) admixing the other ingredients at step (i) with the temporary filtrate at step (vi) in predetermined mixing ratio to create a homogeneous mixture; wherein admixing is at temperature 20° C.-25° C.;
(viii) freezing the homogeneous mixture at step (vii) in frozen molds by using an individual quick freezer (IQF) at temperature from 29° C. to −25° C. to create a frozen sap of inflorescence stalk blocks;
(ix) freeze-drying the frozen sap of inflorescence stalk blocks at step (viii) at a pressure of $7.8948 \times 10^{-4}$–$1.3158 \times 10^{-3}$ atm, and mean while increasing the temperature from (−29° C. to −25° C.) to 60° C. for 48 hours; to obtain a temporary freeze-dried nipa palm powder;
(x) checking if the temporary freeze-dried nipa palm powder at step (ix) is defective or not;
if the temporary freeze-dried nipa palm powder at step (ix) has at least one of the following characteristics including: crumbled and dusty, recrystallization, and moisture content is not less than 4%, then do step (xi);
otherwise, if the temporary freeze-dried nipa palm powder at step (ix) does not have said characteristics, then to obtain a freeze-dried nipa palm powder; and
(xi) grinding the freeze-dried nipa palm powder having at least one of said characteristics at step (x) to obtain a recycling mixture;
wherein the recycling mixture is reused by mixing with the temporary filtrate, and then do step (vii);
wherein a mixing ratio between the temporary filtrate and the recycling mixture is (96-99): (1-4).

2. The method of claim 1, wherein the homogeneous mixture at step (vii) comprising:
100 part of the sap of inflorescence stalk;
0 part the fruit ingredient;
0 part the ginger ingredient; and
0 part the probiotic ingredient.

3. The method of claim 1, wherein the homogeneous mixture at step (vii) comprising:
(75-90) part of the sap of inflorescence stalk;
(10-25) part the fruit ingredient;
0 part the ginger ingredient; and
0 part the probiotic ingredient.

4. The method of claim 1, wherein the homogeneous mixture at step (vii) comprising:
(95-100) part of the sap of inflorescence stalk;
0 part the fruit ingredient;
(1-5) part the ginger ingredient; and
0 part the probiotic ingredient.

5. The method of claim 1, wherein the homogeneous mixture at step (vii) comprising:
100 part of the sap of inflorescence stalk;
0 part the fruit ingredient;
0 part the ginger ingredient; and
(0.1-0.7) part the probiotic ingredient.

6. The method of claim 1, wherein the homogeneous mixture at step (vii) comprising:
(75-90) part of the sap of inflorescence stalk;
(10-25) part the fruit ingredient;
0 part the ginger ingredient; and
(0.1-0.7) part the probiotic ingredient.

7. The method of claim 1, wherein the collecting the sap of inflorescence stalk is at the frequency of 4 times/day.

8. The method of claim 1, wherein the frequency of the collecting the sap of inflorescence stalk is 02 times/day including the first time of collecting at 5:30 am, and the second time at 4:30 pm;
wherein at the first time adding 0.2 g of sodium metabisulfite into the PE bags before using the PE bags to cover the cut position of head of the inflorescence stalk; and
wherein at the second time adding 0.25 g of sodium metabisulfite into the PE bags before used the PE bags to cover the position of the the cut position of head of the inflorescence stalk.

9. The method of claim 1, wherein the frequency of the collecting the sap of inflorescence stalk is 03 times/day including the first time of collecting at 5:30 am, the second time at 10:30 am, and the third time at 4:30 pm;
wherein at the first time and the second time, adding 0 g of sodium metabisulfite into the PE bags before using the PE bags to cover the the cut position of head of the inflorescence stalk; and
wherein at the third time adding 0.25 g of sodium metabisulfite into the PE bags before using the PE bags to cover the position of the head of the said cut the inflorescence.

10. The method of claim 1, wherein the frequency of the collecting the sap of inflorescence stalk is 04 times/day including the first time of collecting at 5:30 am, the second time at 9:30 am, the third time at 1:30 pm, and the fourth time at 4:30 pm;
wherein at the first time, the second time and the third time adding 0 g of sodium metabisulfite into the PE bags before using the PE bags to cover the the cut position of head of the inflorescence stalk; and
wherein at the fourth time adding 0.25 g of sodium metabisulfite into the PE bags before using the PE bags to cover the the cut position of head of the inflorescence stalk.

* * * * *